United States Patent [19]

Pralus et al.

[11] 4,026,908
[45] May 31, 1977

[54] CATALYTIC EPOXIDATION PROCESS

[75] Inventors: Michèle Pralus, Lyon; Jean-Pierre Schirmann, Oullins; Serge-Yvon Delavarenne, Francheville le Haut, all of France

[73] Assignee: Produits Chimiques Ugine Kuhlmann, Paris, France

[22] Filed: Apr. 19, 1976

[21] Appl. No.: 678,129

[30] Foreign Application Priority Data

Apr. 18, 1975 France .................. 75.12061

[52] U.S. Cl. .................. 260/348.5 L; 252/468; 252/475
[51] Int. Cl.² ........................... C07D 301/12
[58] Field of Search .................. 260/348.5 L

[56] References Cited

UNITED STATES PATENTS

| | | | |
|---|---|---|---|
| 3,806,467 | 4/1974 | Watanabe et al. | 252/429 R |
| 3,953,480 | 4/1976 | Delavarenne et al. | 260/348.5 L |

*Primary Examiner*—Norma S. Milestone
*Attorney, Agent, or Firm*—Pennie & Edmonds

[57] ABSTRACT

The present invention relates to a new process for the catalytic epoxidation of olefins which comprises reacting an olefin of the formula

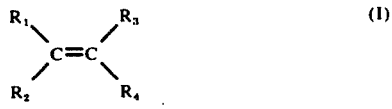

in which $R_1$, $R_2$, $R_3$ and $R_4$, which can be the same or different, represent either a hydrogen atom, a straight alkyl radical having 1 to 30 carbon atoms, a branched alkyl radical or cycloalkyl radical having 3 to 12 carbon atoms, a hydrocarbon radical having 6 to 12 carbon atoms and containing a phenyl group; or $R_1$ and $R_2$, or $R_3$ or $R_4$ together represent a straight or branched alkylene radical with 3 to 11 carbon atoms, (the radicals $R_1$, $R_2$, $R_3$ and $R_4$ can be unsaturated and/or substituted with functional groups which are stable in the reaction medium, such as hydroxy, chloro, fluoro, bromo, iodo, nitro (—$NO_2$), nitroso (—NO), alkoxy, (—OR') amino (—$NH_2$), carbonyl (=CO), alkylcarbonyl

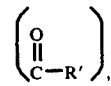

carboxylic acid (—COOH), carboxylic acid ester (—COOR'), amide or carbamyl (—$CONH_2$), nitrile or cyano (—CN) groups, etc.), with hydrogen peroxide at a pH of between about 6 and 9 in the presence of a catalytic system containing at least one derivative of mercury and at least one derivative of the elements IVA, VA, VIA of the Mendeleev Periodic Table. The two fundamental constituents of the catalyst may either belong to distinct molecules or may form part of the same molecule, for example within a complex.

9 Claims, No Drawings

CATALYTIC EPOXIDATION PROCESS

DESCRIPTION OF THE PRIOR ART

The oldest industrial technique for the epoxidation of double bonds is the process known as the chlorohydrin process. The process is not without its drawbacks, particularly because of the simultaneous production of calcium chloride as a by-product of the dehydrochlorination of the chlorohydrin which is difficult to utilize economically.

It is known on the other hand that ethylene may be epoxidized with good yields in the vapour phase by means of molecular oxygen over a catalyst on a silver base. However, this technique is not very useful for the other olefins because of its lack of selectivity therefor.

Other epoxidation processes have therefore been proposed which carry out the oxidation with air in two stages. For example in U.S. Pat. No. 3,351,635 one oxidizes a hydrocarbon such as isobutane or ethyl benzene with air to form the corresponding hydroperoxide. This hydroperoxide is then reacted with the olefin in the presence of a compound of vanadium, molybdenum or tungsten to obtain the epoxide. However, this process has the drawback of producing an alcohol as a by-product of the reaction in a quantity equivalent to the epoxidized compound formed and which is difficult to utilize economically.

Processes have also been proposed which make use of hydrogen peroxide as the oxidizing agent in the presence of a catalyst such as tungstic acid or in the presence of a nitrile such as in U.S. Pat. No. 3,053,856. These two processes also are not satisfactory because in the former case one obtains not the epoxide but the corresponding glycol, whereas in the latter case there is formed, in addition to the epoxide, an equivalent quantity of the amide corresponding to the initial nitrile. The economic interest of such a process is therefore greatly bound up with the possibility of economically utilizing this amide by-product.

Belgian Pat. No. 747,316 discloses the use of hydrogen peroxide as an epoxidizing agent in the presence of a catalyst on a base of an organic derivative of tin. It is difficult, however, to utilize this process on an industrial scale.

In French Pat. No. 2,245,582 of April 3, 1975, the applicants have described a process for the epoxidation of an olefin by means of hydrogen peroxide in the presence of a catalytic system containing at least one derivative of lead and at least one derivative of the elements of Groups IVA, VA, VIA of the Mendeleev Periodic Table.

In U.S. patent application Ser. No. 655,529, filed on Feb. 5, 1976 and assigned to the same assignee as is the instant application, there are described methods of epoxidation comprising reacting the olefins with hydrogen peroxide in the presence of a catalytic system comprising, at least one derivative of arsenic, antimony or bismuth and at least one derivative of elements belonging to groups IVA, VA and VIA of the Mendeleev Periodic Table of Elements. The catalytic systems of particular interest are the organometallic derivatives of metals represented in the first component of the two catalytic systems referred to above in the French patent and French application.

It has now been observed that the use of another type of derivative, that is, the organometallic mercury derivatives, as epoxidation catalyst, instead of the lead, arsenic, antimony or bismuth derivatives as a first component, are more stable and have a longer life than those of the catalytic systems prepared according to French Pat. No. 2,245,582 and U.S. patent application Ser. No. 655,529.

SUMMARY OF THE DISCLOSURE

The object of the present invention is to provide a new catalytic process of epoxidation by means of hydrogen peroxide characterized by the use of a novel catalytic system utilizing derivatives of mercury.

The new catalyst system is formed by the combination of:

1. as a first constituent, at least one inorganic or organic derivative or compound of mercury, and
2. at least one second constituent chosen from among the inorganic or organic derivatives of the transition elements of Groups IVA, VA, VIA of the Mendeleev Periodic Table, and more particularly from among the derivatives of vanadium, molybdenum, tungsten, and titanium.

Such a catalytic system has a longer working life and a good selectivity for epoxidation of a wide variety of olefins.

The association of the two fundamental constituents may be achieved either by the addition to the reaction medium of two distinct molecules which may act together or react with one another to give an active catalytic system, or by a single molecule grouping the two constituents together such as in a complex.

DETAILED DESCRIPTION OF THE INVENTION

The present invention relates to a new process for catalytic epoxidation of olefins. Examples of olefins which can be catalytically epoxidized according to the invention include those of the formula:

in which $R_1$, $R_2$, $R_3$ and $R_4$, which can be the same or different, represent either a hydrogen atom, a straight alkyl radical having 1 to 30 carbon atoms, a branched alkyl radical or cycloalkyl radical having 3 to 12 carbon atoms, a hydrocarbon radical having 6 to 12 carbon atoms and containing a phenyl group; or $R_1$ and $R_2$, or $R_3$ or $R_4$ together represent a straight or branched alkylene radical with 3 to 11 carbon atoms, such as cyclohexene (the radicals $R_1$, $R_2$, $R_3$ and $R_4$ can be unsaturated and/or substituted with functional groups which are stable in the reaction medium, such as hydroxy, chloro, fluoro, bromo, iodo, nitro (—$NO_2$), nitroso (—NO), alkoxy (—OR′), amino (—$NH_2$), carbonyl (=CO), alkylcarbonyl

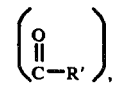

carboxylic acid (—COOH), carboxylic acid ester (—COOR′), amide or carbamyl (—$CONH_2$), nitrile or cyano (—CN) groups, etc), with hydrogen peroxide at a pH of between about 6 and 9 in the presence of a catalytic system containing at least one derivative of mercury and at least one derivative of the elements of groups IVA, VA, VIA of the Mendeleev Periodic Table. The two fundamental constituents of the catalyst may either belong to distinct molecules or may form part of the same molecule, for example within a complex.

Examples of mercury derivatives that can be used according to the invention includes the oxides, hydroxides, salts derived from mineral hydracids and oxyacids or aromatic or aliphatic carboxylic or sulfonic acids containing not more than about 20 carbons atoms, and mixed derivatives thereof, and whose anions are stable under the reaction conditions. By way of more specific examples one may cite mercury fluoride, chloride, nitrate, sulfate, phosphate, pyrophosphate, polyphosphate, borate, carbonate, formate, acetate, propionate, butyrate, isobutyrate, hexanoate, octanoate, dodecanoate, naphthenate, stearate, oxalate, succinate, glutarate, adipate, benzoate, phthalate, methanesulfonate, ethanesulfonate, benzenesulfonate, p-toluenesulfonate, etc. These salts may be used as such or they may also be formed in situ, starting from the hydroxide and adding the corresponding acid.

Other derivatives of mercury can be used and can correspond to the following general formula:

 (II)

in which $n$ and $m$ are whole numbers having a value of 0–2 and in which $n + m = 2$ and in which the R groups, which may be identical or different, represent either a hydrogen atom, a straight alkyl radical having 1 to 12 carbon atoms, a branched alkyl radical or cycloalkyl radical having 3 to 12 carbon atoms, or a hydrocarbon radical having from 6 to 12 carbon atoms and containing a phenyl group or, in cases where $n = 2$ the groups R may represent together a straight alkylene group with 3 to 11 carbon atoms. These radicals R can, if desired, be substituted with functional groups which are stable in the reaction medium, such as hydroxy, chloro, fluoro, bromo, iodo, nitro (—NO$_2$), nitroso (—NO), alkoxy (OR''), amino (—NH$_2$), carbonyl =CO), alkylcarbonyl

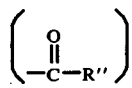

carboxylic acid (—COOH), carboxylic acid ester (—COOR''), amide or carbamyl (—CONH$_2$), nitrile or cyano (—CN) groups, etc. The groups X, which may be the same or different, represents either a hydroxyl group, a halogen group, an oxygen atom, the anion of a mineral oxyacid a mineral hydracid or an organic oxyacid, or an ether group OR, or an —O—HgR group in which R has the same meaning as given above. The organic oxyacids are preferably carboxylic acids or aliphatic or aromatic sulfonic acids containing not more than about 20 carbon atoms. The representation of R'' above is not critical so long as it does not interfere with the catalytic activity of the mercury catalyst. R'' is preferably a lower alkyl radical containing from about 1 to 6 carbon atoms.

The following may be cited by way of nonlimitative examples of mercury derivatives of formula II which may be used within the scope of the present invention: alkyl mercury hydroxides, aryl mercury hydroxides, and the fluorides, chlorides, bromides, iodides, nitrates, acid sulfates, neutral sulfates, mono-, di- and triphosphates, pyrophosphates, polyphosphates, borates, carbonates, triophosphates, arsenates, titanates, vanadates, selenates, molybdates, tungstates, formates, acetates, propionates, butyrates, isobutyrates, hexanoates, octanoates, dodecanoates, stearates, oxalates, succinates, glutarates, adipates, benzoates, phthalates, acetylacetonates, methanesulfonates, ethanesulfonates, benzenesulfonates, p-toluenesulfonates, etc. of monoalkyl or monoaryl mercury; the monoalkyl or monoaryl methoxy, ethoxy or phenoxy mercury derivatives.

The compounds or derivatives of mercury which form the first constituent are used, of course, in their existent valent states. They may be used as such but it is also possible to prepare them in situ from other derivatives of mercury. The amount of the mercury derivative is preferably chosen between about 0.01 and 10% by weight of the total reaction mixture, and more advantageously between about 0.1 and 2%.

The second constituent of the catalytic system is at least one mineral or organic derivative of the transition metals of Groups IVA, VA and VIA of the Mendeleev Periodic Table of Elements. Derivatives of vanadium, molybdenum, tungsten and titanium are most advantageous. Some examples of organic derivatives include the naphthenates, acetylacetonates, stearates, octoates, carbonyl derivatives, polyacids, etc. of the metals mentioned above. Some examples of mineral derivatives are the oxides, the derivatives of mineral hydracids and oxyacids and their salts, such as the phosphates, nitrates, sulphates, carbonates, arsenates, etc. Many other mineral or organic derivatives which are well known in the art can, or course, be used.

The quantity of this second constituent of the catalyst is preferably selected to be between about 0.01 and 10% by weight of the total reaction mixture and more advantageously between about 0.1 and 1%. The two basic components of the catalyst may belong to different molecules, but can also form part of the same molecule. For example it is possible to use, within the scope of the present invention, compounds such as phenyl mercury tungstate or molybdate. It is also possible to use composite salts containing one of the elements molybdenum, tungsten, vanadium, titanium, etc., e.g. phosphotungstic acid, phosphomolybdic acid, phosphovandic acid and their salts, particularly their monoalkyl or monoaryl mercury salts. The two basic components of the catalyst may also be found within a single complex compound, e.g, [C$_p$M(CO$_3$)$_n$HgR$_m$, where C$_p$ represents a cyclopentadienyl group, M is W or Mo, $m = n = 2$, and R is defined as above.

Some more specific examples of olefins which may be epoxidized by the process of the invention include, by way of non-restrictive examples, ethylene, propylene, the butenes, butadiene, the pentenes, hexane-1, hexane-3, heptene-1, octene-1, octene-2, diisobutylene, nonene-1, decene-1, limonene, pinene, myrcene, camphene, undecene-1, dodecene-1, tridecene-1, tetradecene-1, nonadecene-1, pentadecene-1, hexadecene-1, heptadecene-1, octadecene-1, eicosene-1, the trimers and tetramers of propylene, the polybutadienes, styrene, -methylstyrene, divinylbenzene, indene, stilbene, cyclopentene, cyclohexene, cycloheptene, cyclooctene, cyclooctadiene, cyclododecene, cyclododecatriene, dicyclopentadiene, vinylcyclohexane, methylallylketone, allyl chloride, allyl bromide, methacrylic acid, acrylic acid, crotonic acid, vinylacetic acid, crotyl chloride, methallyl chloride, the dichlorobutenes, allyl alcohol, allyl carbonate, allyl acetate, alkylmethacrylates, acrylates, diallylmaleate, dialkylphthalate, unsaturated glyacids, such as soya bean oil, sunflower seed oil, corn oil, cotton seed oil, olive oil, castor oil, ground nut oil (peanut oil), tall oil, tallow oil and linseed oil, unsaturated fatty acids such as oleic, linolenic, balidic, erucic, oleostearic, myristoleic, palmitoleic, licanic, ricinoleic, arachidonic acids, etc., as well as their esters.

The preferred mode of operation for epoxidizing ethylenic compounds according to the process of the invention comprises reacting the two reagents, the olefin and hydrogen peroxide in the presence of the catalyst in aqueous solution or in the presence of a solvent which facilitates the homogenization of the mixture. This solvent may be either an aliphatic-monoalcohol containing 1 to 4 carbon atoms, for example, methanol, ethanol, n-propanol, isopropanol, n-butanol, isobutanol, secondary butanol, tert-butanol, or a nitrile such as acetonitrile, or an amide such as dimethylformamide or an ether such as dioxan or tetrahydrofuran. One may also operate without a solvent in a non-homogeneous medium in the presence of water.

The reaction can be carried out at atmospheric pressure or under a pressure which may range up to 100 bars if this is necessary to maintain the olefin dissolved in the reaction medium. The preferred temperature is between 50° and 100° C. The apparent pH of the medium is preferably maintained at between about 6 and 9 and advantageously between about 7 and 8.

The pH of the reaction medium may be adjusted, if necessary, by the addition either of a base, preferably chosen from among the hydroxides or carbonates of the alkali or alkali earth metals, or an acid which is preferably selected from mineral hydracids or oxyacids, such as hydrochloric acid, sulphuric acid, phosphoric acid, or the aliphatic or aromatic carboxylic or alkyl or aryl sulphonic acids having less than about 20 carbon atoms.

The duration of the reaction depends on the catalytic system used as well as the nature of the olefin employed. It may range from a few minutes up to 100 hours and over.

The olefins and hydrogen peroxide may be used in equimolecular quantities, but it is also possible to use a molar deficit or excess of one or the other. By way of guidance it is possible to use from 0.1 to 5 moles of olefin per mole of hydrogen peroxide, but it is preferable to use 1 to 2 moles of olefin per mole of $H_2O_2$. The reactants may be used in their usual commercial form. In particular, hydrogen peroxide may be used in aqueous solutions containing 30 to 90% by weight of $H_2O_2$.

The reactants and the catalyst may be introduced into the reaction medium simultaneously or in any order of sequence. It is preferable to add the reagents gradually and at a temperature to maintain an effective control of the thermal effects of the reaction.

It may be advantageous to add to the reaction mixture known compounds which stabilize hydrogen peroxide, such as phosphoric acid, nitrilotriacetic acid, ethylenediaminetetracetic acid or their sodium salts.

The uses of the epoxides produced according to this invention are well known. They can be used, for example, to form homopolymers or copolymers (with bis-phenol A, for example, to form bis-phenol A "epoxide resins") to prepare plasticizers and other useful products as is well known in the art.

The following Examples illustrate the present invention. The selectivity is defined as the number of moles of epoxide formed, reckoned on the number of moles of hydrogen peroxide which have taken part in the reaction.

Example 1

0.14 g of methylmercury hydroxide $CH_3HgOH$ (0.6 millimole), 11 g of acetonitrile, 4.1 g of cyclohexene (50 millimoles, 0.1 g of tungsten hexacarbonyl and 1.46 g of aqueous hydrogen peroxide solution, 70% by weight (30 millimoles) are agitated in a reactor maintained at 70°. After four hours of reaction the reaction mixture is analyzed by gas chromatography, which shows the presence of 1.56 g of epoxycyclohexane (15.9 millimoles) which for an 89% conversion of hydrogen peroxide corresponds to an epoxide selectivity of 62%.

Example 2

Example 1 is repeated except that the acetonitrile is replaced with 11 g of n-propanol. 17.56 millimoles of epoxycyclohexane are formed, corresponding to a selectivity of 63% for a 92% conversion of hydrogen peroxide.

Example 3

Example 1 is repeated except that the $CH_3HgOH$ is replaced with $(CH_3Hg)_2PO_4H$. 23.3 millimoles of epoxycyclohexane are formed, corresponding to a selectivity of 87% for a 90% conversion of the hydrogen peroxide.

EXAMPLE 4

Example 3 repeated excepted that the $W(CO)_6$ is replaced with $Mo(CO)_6$. 13.9 millimoles of epoxycyclohexane are formed, corresponding to a selectivity of 51% for a 90% conversion of the hydrogen peroxide.

EXAMPLE 5

A mixture of 11 g of propanol, 4.1 g of cyclohexane (50 millimoles), 0.175 g of phenylmercury hydroxide $C_6H_5HgOH$ (0.6 millimole), 0.1 g of tungsten hexacarbonyl and 1.4 g of an aqueous solution of hydrogen peroxide, 70% by weight (30 millimoles) is heated to 70° C. After 4 hours of reaction, gas chromatography analysis shows the presence of 1.57 g of epoxycyclohexane (16 millimoles), which for an 84% conversion of hydrogen peroxide and corresponds to an epoxide selectivity of 65%.

Example 6

Example 5 is repeated except that the phenylmercury hydroxide is replaced with 0.148 g of ethylmercury hydroxide (0.6 millimole). 13.7 millimoles of epoxycyclohexane are formed, which corresponds to a selectivity of 46% for a 100% conversion of hydrogen peroxide.

EXAMPLE 7

A mixture of 0.160 of $(CH_3Hg)_2PO_4H$ (0.3 millimole), 0.1 g of tungsten hexacarbonyl, 4.1 g of cyclohexene (50 millimoles), 1.46 g of aqueous hydrogen peroxide solution, 70% by weight (30 millimoles) and 11 g of tert-butanol are reacted for 15 hours at 70° C, Gas chromatography analysis shows the presence of 18.0 millimoles of epoxycyclohexane, which corresponds to a selectivity of 68% for an 83% conversion of hydrogen peroxide.

Example 8

Example 7 is repeated except that the solvent tert-butanol is replaced with 11 g of isopropanol. In this case 18.2 millimoles of epoxycyclohexane are analyzed by gas chromatography which corresponds to a selectivity of 74% for an 82% conversion of hydrogen peroxide.

Example 9

Example 7 is repeated except that the tert-butanol is replaced with 20 g of dioxane. Under these conditions an amount of epoxycyclohexane is formed which for a 32% conversion of the hydrogen peroxide corresponds to a selectivity of 45%.

Example 10

Example 7 is repeated except that the tert-butanol is replaced with 20 g of tetrahydrofuran. Gas chromatography analysis shows the presence of 11.2 millimoles of epoxycyclohexane, which corresponds to a selectivity of 50% for a 75% conversion of the hydrogen peroxide.

Example 11

A mixture of 0.160 g of $(CH_3Hg)_2PO_4H$ (0.3 millimole), 11 g of acetonitrile, 4.1 g of cyclohexene (50 millimoles), 0.1 g of tungsten dioxide $WO_2$ and 14.6 g of aqueous hydrogen peroxide solution, 70% by weight (30 millimoles) is agitated in a reactor maintained at 70° C. After 4 hours of reaction gas chromatography analysis shows the presence of 6.9 millimoles of epoxycyclohexane, which corresponds to a selectivity of 41% for a 56% conversion of the hydrogen peroxide.

Example 12

A mixture of 11 g of acetonitrile, 4.1 g of cyclohexene (50 millimoles), 0.13 g of mercuric oxide HgO (0.6 millimole), 0.1 g of tungsten hexacarbonyl and 14.6 g of an aqueous solution of hydrogen peroxide, 70% by weight (30 millimoles) is heated to 70° C. After 4 hours of reaction, gas chromatography analysis shows presence of 1.08 g of epoxycyclohexane (11 millimoles), representing a selectivity of 41% for an 89% conversion of the hydrogen peroxide.

Example 13

Example 12 is repeated except that the mercuric oxide is replaced with 0.178 g of mercuric sulfate $HgSO_4$. Under these conditions an amount of epoxycyclohexane is formed representing a selectivity of 30% for a 91% conversion of the hydrogen peroxide.

Example 14

A mixture of 20 g of acetonitrile, 5.2 g of styrene (50 millimoles), 1.46 g of aqueous hydrogen peroxide solution, 70% by weight (30 millimoles), 0.16 g of $(CH_3Hg)_2PO_4H$ and 0.1 g of tungsten hexacarbonyl is reacted for 4 hours at 70° C. Gas chromatography analysis shows the presence of 2.52 g of the epoxidized styrene (21 millimoles) which corresponds to a selectivity of 80% for an 84% conversion of the hydrogen peroxide.

Example 15

Example 14 is repeated except that the styrene is replaced with 5.6 g of octene-1 (50 millimoles). Gas chromatography analysis shows the presence of 1.15 g of epoxidized octene-1 (9 millimoles) which corresponds to a selectivity of 82% for a 36% conversion of the hydrogen peroxide.

Example 16

A mixture of 30 g of propanol, 10 g of aqueous hydrogen peroxide solution, 70% by weight, 0.16 g of $(CH_3Hg)_2PO_4H$ and 0.1 g of tungsten hexacarbonyl is heated to 30° C. Propylene is bubbled into this stirred mixture. After 4 hours of reaction gas chromatography analysis is carried out, showing the presence of 0.9 g of propylene oxide (16 millimoles), which corresponds to a selectivity of 58% for a 14% conversion of the hydrogen peroxide.

Example 17

A mixture of 0.17 g of $(CH_3Hg)_2PO_4H$ (0.3 millimole), 20 g of acetonitrile, 4.1 g of cyclohexane (50 millimoles), 0.1 g of molybdyl acetylacetonate and 30 millimoles of aqueous hydrogen peroxide solution, 70% by weight, is stirred in a reactor maintained at 70° C. After 4 hours of reaction, gas chromatography analysis shows the presence of 12.7 millimoles of epoxycyclohexane, which corresponds to a selectivity of 62% for a 68% conversion of hydrogen peroxide.

Example 18

Example 17 is repeated except that the molybdyl acetylacetonate is replaced with 0.1 g of molybdenum napthenate. Gas chromatography analysis shows the presence of 1.5 millimoles of epoxycyclohexane which corresponds to a selectivity of 35% for a 14% conversion of the hydrogen peroxide.

We claim:
1. The process of epoxidizing an olefin which comprises reacting an olefin with hydrogen peroxide at a pH between about 6 and 9 in the presence of a catalytic amount of (1) at least one compound of mercury and (2) at least one compound of the elements vanadium, molybdenum, tungsten or titanium, or complexes of (1) and (2).

2. The process of claim 1 in which the olefin being epoxidized corresponds to the general formula

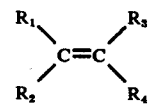

in which $R_1$, $R_2$, $R_3$ and $R_4$, which are the same or different, represent either a hydrogen atom, a straight alkyl radical containing 1 to 30 carbon atoms, a branched alkyl radical or cycloalkyl radical containing 3 to 12 carbon atoms, or a hydrocarbon radical containing 6 to 12 carbon atoms and containing a phenyl group, or $R_1$ and $R_2$ or $R_3$ or $R_4$ together represent a straight or branched alkylene radical with 3 to 11 carbon atoms, the radicals $R_1$, $R_2$, $R_3$ and $R_4$ can be unsaturated and/or substituted by hydroxy, chloro, fluoro, bromo, iodo, nitro, nitroso, alkoxy, amino, carbonyl, carboxyl acid, carboxyl acid ester, amide or nitrile functional groups stable in the reaction medium.

3. The process of claim 2 in which the derivatives are mixed organo-inorgano derivatives.

4. Process according to claim 1, wherein the mercury catalyst (1) is a mercury derivative having the formula $(R)_nHgX_m$, where $n$ and $m$ are whole numbers which range from 0 to 2 and in which $n + m = 2$, and where the R groups, which may be different or identical, each represent either a hydrogen atom, a linear alkyl radical containing 1 to 12 carbon atoms, a branched alkyl radical or cycloalkyl radical containing 3 to 12 carbon atoms, or a hydrocarbon radical containing 6 to 12 carbon atoms and containing a phenyl group; or in the case where $n = 2$ the R groups together represent a linear alkylene group containing 3 to 11 carbon atoms, and which R groups can be substituted with the functional groups hydroxyl, chloro, fluoro, bromo, iodo, nitro, nitroso, methoxy, alkoxy, amino, carbonyl, alkylcarbonyl, carboxylic acid, carboxylic acid ester, amide, or nitrile groups which groups are stable in the reaction medium and where X, which may be identical or different, represent a hydroxyl group, an oxygen atom, a halogen atom, the anion of a mineral oxyacid, mineral hydracid, or the anion of an organic oxyacid containing less than about 20 carbon atoms, an O—R ether group, or an —O—HgR group where R has the meaning defined above.

5. Process according to claim 4 wherein the reaction takes place at a temperature between about 50° and 100° C.

6. Process according to claim 4, wherein catalyst (1) is present in an amount between about 0.1 to 2% of the weight of the total reaction mixture, and catalyst (2) is present in an amount between about 0.1 to 1% of the weight of the total reaction mixture.

7. Process according to one of claim 4, wherein the reaction takes place in a solvent medium.

8. Process according to claim 7 wherein the solvent is an aliphatic alcohol containing 1 to 4 carbon atoms.

9. Process according to claim 7, wherein the solvent is an aliphatic nitrile containing 2 to 5 carbon atoms.

* * * * *

UNITED STATES PATENT AND TRADEMARK OFFICE
CERTIFICATE OF CORRECTION

PATENT NO. : 4,026,908
DATED : May 31, 1977
INVENTOR(S) : Michele Pralus, Jean-Pierre Schirmann, Serge-Yvon Delavarenne It is certified that error appears in the above-identified patent and that said Letters Patent are hereby corrected as shown below:

Column 4, lines 50-51, "m = n = 2," should read --m + n = 2,--.

Column 4, line 65, "vinylcyclohexane" should read --vinylcyclohexene--.

Column 6, line 10, "(50 millimoles," should read --(50 millimoles),--.

Column 6, line 62, "0.160 of" should read --0.160 g of--.

Column 7, line 29, "14.6 g" should read --1.46 g--.

Column 7, line 40, "14.6 g" should read --1.46 g--.

Column 8, line 19, "cyclohexane" should read --cyclohexene--

Signed and Sealed this

Twenty-seventh Day of September 1977

[SEAL]

Attest:

RUTH C. MASON
*Attesting Officer*

LUTRELLE F. PARKER
*Acting Commissioner of Patents and Trademarks*